US007575897B2

(12) United States Patent
Scheiflinger et al.

(10) Patent No.: US 7,575,897 B2
(45) Date of Patent: Aug. 18, 2009

(54) HIGHLY PHOSPHORYLATED AND SULFATED RECOMBINANT FACTOR IX

(75) Inventors: Friedrich Scheiflinger, Vienna (AT); Ernst Boehm, Vienna (AT); Michele Himmelspach, Port (CH); Olaf Merkel, Salzburg (AT)

(73) Assignees: Baxter International, Inc., Deerfield, IL (US); Baxter Healthcare S.A., Zurich (CH)

( * ) Notice: Subject to any disclaimer, the term of this patent is extended or adjusted under 35 U.S.C. 154(b) by 0 days.

(21) Appl. No.: 12/058,473

(22) Filed: Mar. 28, 2008

(65) Prior Publication Data

US 2008/0176287 A1    Jul. 24, 2008

Related U.S. Application Data

(63) Continuation of application No. 11/683,362, filed on Mar. 7, 2007, now Pat. No. 7,375,084.

(60) Provisional application No. 60/789,857, filed on Apr. 5, 2006, provisional application No. 60/779,830, filed on Mar. 7, 2006.

(51) Int. Cl.
*C12P 21/06* (2006.01)
(52) U.S. Cl. .................................. 435/69.1
(58) Field of Classification Search ............... 435/6
See application file for complete search history.

(56) References Cited

FOREIGN PATENT DOCUMENTS

| EP | 0 669 342 B1 | 2/1995 |
| WO | WO 94/20078 A1 | 9/1994 |
| WO | WO 94/23701 A1 | 10/1994 |
| WO | WO 96/06638 A1 | 3/1996 |

OTHER PUBLICATIONS

Altschul, Stephen, et al., "Basic Local Alignment Search Tool," J. Mol. Biol., 1990, vol. 215, pp. 403-410.
Altschul, Stephen, et al., "Gapped BLAST and PSI-BLAST: a new generation of protein database search programs," Nucleic Acids Research, 1997, vol. 25, No. 17, pp. 3389-3402.
Arruda, Valder, et al., "Posttranslational modifications of recombinant myotube-synthesized human factor IX," Blood, 2001, vol. 97, No. 1, pp. 130-138.
Autin, et al., "Molecular models of the procoagulant factor VIIIa-factor IXa complex," Journal of Thrombosis and Haemostasis, 2005, vol. 3, No. 9, pp. 2044-2056.
Björkman, S., et al., "Pharmacokinetics of recombinant factor IX in relation to age of the patient: implications for dosing in prophylaxis," Haemophilia, 2001, vol. 7, pp. 133-139.

Bond, M. et al., "Biochemical Characterization of Recombinant Factor IX," Seminars in Hematology, 1998, vol. 35, No. 2, Suppl 2., pp. 11-17.
Brinkhous, Kenneth, et al., "Recombinant Human Factor IX: Replacement Therapy, Prophylaxis, and Pharmacokinetics in Canine Hemophilia B," 1996, vol. 88, No. 7, pp. 2603-2610.
Chen, CC, et al., "The aPTT assay as a monitor of heparin anticoagulation efficacy in clinical settings," Adv. Ther., 2003, vol. 20, No. 5, pp. 231-236.
Choo, K.H. "Molecular cloning of the gene for human anti-haemophilic factor IX," Nature, 1982, vol. 299, pp. 178-180.
Coombes AG, et al., "Single dose, polymeric, microparticle-based vaccines: the influence of formulation conditions on the magnitude and duration of the immune response to a protein antigen," Vaccine, 1996, vol. 14, No. 15 pp. 1429-1438.
Ewenstein, B.M., et al., "Pharmacokinetic analysis of plasma-derived and recombinant F IX concentrates in previously treated patients with moderate or severe hemophilia B," Transfusion, 2002, vol. 42, No. 2, pp. 190-197.
Harrison, S, et al., "The Manufacturing Process for Recombinant Factor IX," Seminars in Hematology, 1998, vol. 35, No. 2, Suppl 2, pp. 4-10.
Henikoff, Steven, et al., "Amino Acid Substitution Matrices from Protein Blocks," Proc. Natl. Acad. Sci. USA, 1992, vol. 89, pp. 10915-10919.
Herlitschka, Sabine, et al., "Overexpression of Human Prothrombin in Permanent Cell Lines Using a Dominant Selection/Amplification Fusion Marker," Protein Expression and Purification, 1996, vol. 8, pp. 358-364.
Jaye, Michael, et al., "Isolation of a human anti-haemophilic factor IX cDNA clone using a unique 52-base synthetic oligonucleotide probe deduced from the amino acid sequence of bovine factor IX," 1983, Nucleic Acids Research, vol. 11, No. 8, pp. 2325-2335.
Kaufman, Randal, et al., "Expression, Purification, and Characterization of Recombinant γ-Carboxylated Factor IX Synthesized in Chinese Hamster Ovary Cells," The Journal of Biological Chemistry, 1986, vol. 261, No. 21, pp. 9622-9628.
Kaufman, Randal. et al., "Post-translational Modification Required for Coagulation Factor Secretion and Function," Thromb Haemost, 1998, vol. 79, pp. 1068-1079.
Keith, James., et al., "Evaluation of Recombinant Human Factor IX: Pharmacokinetic Studies in the Rat and the Dog," Trombosis and Haemostasis, 1995, vol. 73, pp. 101-105.
Kisker, C.T., et al., "Prophylaxis in factor IX deficiency product and patient variation," Haemophilia, 2003, vol. 9, pp. 279-284.
Kurachi, Kotoku, et al., "Isolation and characterization of a cDNA coding for human factor IX," Proc. Natl. Acad. Sci. USA, 1982, vol. 79, pp. 6461-6464.
Mammalian Gene Collection (MGC) Program Team, "Generation and initial analysis of more than 15,000 full-length human and mouse cDNA sequences," PNAS, 2002, vol. 99, No. 26, pp. 16899-16903.

(Continued)

*Primary Examiner*—Maryam Monshipouri
(74) *Attorney, Agent, or Firm*—Townsend and Townsend and Crew LLP

(57) ABSTRACT

The present invention relates to a purified recombinant blood coagulation factor IX (rFIX) preparation, wherein at least 25% of the rFIX in the preparation is fully phosphorylated and sulfated, a cell culture expressing a rFIX resulting in said preparation, a pharmaceutical composition for treating a bleeding disorder comprising said preparation, and a method for treating a bleeding disorder comprising the step of administering said preparation to a patient in need thereof.

6 Claims, No Drawings

OTHER PUBLICATIONS

McCarthy, K., et al., "Pharmacokinetics of Recombinant Factor IX after Intravenous and Subcutaneous Administration in Dogs and Cynomolgus Monkeys," 2002, Thromb Haemost, vol. 87, pp. 824-830.

McGraw, R.A., et al., "Evidence for a prevalent dimorphism in the activation peptide of human coagulation factor IX," Proc. Natl. Acad. Sci. USA, 1985, vol. 82, pp. 2847-2851.

Needleman, Saul, et al. "A General Method Applicable to the Search for Similarities in the Amino Acid Sequence of Two Proteins," J. Mol. Biol. 1970, vol. 48, pp. 443-453.

Pearson, William, et al., "Improved tools for biological sequence comparison," Proc. Natl. Acad. Sci. USA, 1988, vol. 85, pp. 2444-2448.

Poon, Man-Chiu, "Recombinant Factor IX Recovery and Inhibitor Safety: a Canadian Post-licensure Surveillance Study," Thrombosis and Haemostasis, 2002, vol. 87, pp. 431-435.

Ragni, M.V., et al., "Use of recombinant factor IX in subjects with haemophilia B undergoing surgery," 2002, vol. 8, pp. 91-97.

Rost, Simone, et al., "Mutations in VKORC1 cause warfarin resistance and multiple coagulation factor deficiency type 2," Nature, 2004, vol. 427, pp. 537-544.

Roth, David, et al., "Human recombinant factor IX: safety and efficacy studies in hemophilia B patients previously treated with plasma-derived factor IX concentrates," Blood, 2001, vol. 98, No. 13, pp. 3600-3606.

Scahill, Shaun, et al., "Expression and characterization of the product of a human immune interferon cDNA gene in Chinese hamster overy cells," Proc. Natl. Acad. Sci USA, 1983, vol. 80, pp. 4654-4658.

Schaub, R. et al., "Preclinical Studies of Recombinant Factor IX," Seminars in Hematology, 1998, vol. 35, No. 2, Suppl. 2, pp. 28-32.

Shapiro, A.D., et al., "Use of pharmacokinetics in the coagulation factor treatment of patients with haemophilia," Haemophilia, 2005, vol. 11, pp. 571-582.

Shapiro, Amy, et al., "The safety and efficacy of recombinant human blood coagulation factor IX in previously untreated patients with severe or moderately severe hemophilia B," Blood, 2005, vol. 105. No. 2, pp. 518-525.

Smith, Temple, et al., "Comparison of Biosequences," Advances in Applied Mathematics, 1981, vol. 2., pp. 482-489.

Wasley, Louise, et al. "PACE/Furin Can Process the Vitamin K-dependent Pro-factor IX Precursor within the Secretory Pathway," The Journal of Biological Chemistry, 1993, vol. 268, No. 12, pp. 8458-8465.

White, Gilbert, "Recombinant Factor IX," Thrombosis and Haemostasis, 1997, vol. 78., No. 1., pp. 261-265.

White, Gilbert., "Mammalian Recombinant Coagulation Proteins: Structure and Function," Transfus. Sci., 1998, vol. 19, No. 2, pp. 177-189.

HIGHLY PHOSPHORYLATED AND SULFATED RECOMBINANT FACTOR IX

CROSS-REFERENCES TO RELATED APPLICATIONS

This application claims the benefit of U.S. Provisional Patent Application Nos. 60/779,830, filed Mar. 7, 2006 and 60/789,857, filed Apr. 5, 2006, the disclosures of which are hereby incorporated by reference in their entirety for all purposes, and is a continuation of U.S. Ser. No. 11/683,362, filed Mar. 7, 2007, now U.S. Pat. No. 7,375,084 herein incorporated by reference in its entirety.

REFERENCE TO A "SEQUENCE LISTING," A TABLE, OR A COMPUTER PROGRAM LISTING APPENDIX SUBMITTED ON A COMPACT DISK

Not applicable.

FIELD OF THE INVENTION

The present invention relates to a purified recombinant blood coagulation factor IX (rFIX) preparation having at least 25% and less than 98% of fully phosphorylated and sulfated rFIX, a cell culture expressing a rFIX resulting in said preparation, a pharmaceutical composition for treating a bleeding disorder comprising said preparation, and a method for treating a bleeding disorder comprising the step of administering said preparation to a patient in need thereof.

BACKGROUND OF THE INVENTION

Hemophilia B, a hereditary recessive bleeding disorder, is successfully treated by replacement therapy consisting of the administration of preparations of human plasma derived (pdFIX) or recombinant coagulation factor IX (rFIX). The commercially available recombinant product, which is marketed under the trade name Benefix™, is manufactured by using stable transfected Chinese hamster ovary (CHO) cells co-expressing rFIX together with endopeptidase PACE/Furin, and is highly purified via multiple filtration and chromatographic steps (Kaufman et a., 1986; Wasley et al., 1993; Harrison et a., 1998). In clinical studies, Benefix™ has been shown to be safe and effective, but a 20 to 50% higher dosage than for pdFIX is needed for successful treatment. This is due to a 30 to 50% lower in vivo recovery for CHO derived rFIX than for pdFIX, as revealed by pharmacokinetic data collected from pre-clinical and clinical studies, where pdFIX and rFIX are compared in different animal models (Keith, Jr. et al., 1995; Brinkhous et a., 1996; Schaub et al., 1998; McCarthy et al., 2002), and clinical studies in hemophilia B patients (Keith, Jr. et al., 1995; White et al., 1997; White et al., 1998; Bjorkman et al., 2001; Roth et al., 2001; Ewenstein et al., 2002; Poon et al., 2002; Ragni et al., 2002; Kisker et al., 2003; Shapiro et al., 2005a). The circulating half-life of rFIX is not distinguishable from pdFIX preparations.

Biochemical comparison between pdFIX and CHO derived rFIX revealed differences in post-translational modifications (Bond et al., 1998). The lower degree of phosphorylation of a unique site at the activation-peptide amino acid serine 155 and the lower degree of sulfation of tyrosine 158 have been assigned to the lower in-vivo recovery of rFIX (White et al., 1997; Kaufman, 1998), although experimental evidence to proof this assumption has not been published to-date. These two modifications were identified to occur at less than 15% for the tyrosine-sulfation and at less than 1% for the serine phosphorylation in the recombinant protein, whereas the plasma derived protein has both modifications to more than 90% completed. Similar pharmacokinetic properties to Benefix™ were found for myotube-synthesized rFIX after adeno-associated viral vector mediated gene delivery in a mouse model (Arruda et al., 2001).

Therefore, a strong need exists for a new rFIX preparation which can be administered in a lower dosage than conventional rFIX preparation for a successful treatment.

Thus, it is an object of the present invention to provide a new rFIX preparation, wherein the rFIX has an improved in vivo recovery.

SUMMARY OF THE INVENTION

The present invention relates to a purified recombinant blood coagulation factor IX (rFIX) preparation having at least 25% and less than 98% of fully phosphorylated and sulfated rFIX. The rFIX is for example expressed in a host cell type with the ability to perform the phosphorylation and sulfation as posttranslational modifications. Additionally, a cell culture expressing rFIX resulting in a purified rFIX preparation having at least 25% and less than 98% of fully phosphorylated and sulfated rFIX, e.g. a HEK293-derived cell culture, is provided according to the present invention. Further, the present invention relates to a pharmaceutical composition comprising a purified rFIX preparation having at least 25% and less than 98% of fully phosphorylated and sulfated rFIX for treating a bleeding disorder, e.g. hemophilia B. It is another object of the present invention to provide a method for treating a bleeding disorder comprising the step of administering a pharmaceutical composition comprising a purified rFIX preparation having at least 25% and less than 98% of fully phosphorylated and sulfated rFIX for treating a bleeding disorder.

DETAILED DESCRIPTION OF THE INVENTION

One aspect of the present invention relates to a purified recombinant blood coagulation factor IX (rFIX) having at least 25% of fully phosphorylated and sulfated rFIX. The degree of phosphorylation and sulfation may be identified by determining the percentage of fully phosphorylated and sulfated rFIX by mass spectrometry (MS), e.g., electrospray-ionization quadrupole time of flight mass spectrometry (ESI-QTOF-MS). When measured with ESI-QTOF-MS, the percentage of fully phosphorylated and sulfated rFIX in a plasma derived FIX sample used as a standard is about 98%. For conventional rFIX-preparations, e.g. Benefix™, sulfation degree can be less than 15% and phosphorylation degree less than 1%. Any phosphorylation or sulfation degree leading to an increased in vivo recovery compared to Benefix™ can be determined as high, but at least 25% sulfation and phosphorylation and less than 98% phosphorylation and sulfation is encompassed by the present invention. In one example, the range is 30%-95%, 35%-90%, 40%-85%, 40%-75%, 40%-65%, 40-60%, 40-55%, or 45-50%. In one example of the present invention, the percentage of fully phosphorylated and sulfated rFIX material after purification is at least 28%. In another example of the present invention, the percentage of fully phosphorylated and sulfated rFIX material after purification is at least 35%. In one example of the present invention, the percentage of fully phosphorylated and sulfated rFIX material after purification is at least 46%. In one further example of the present invention, the percentage of fully phosphorylated and sulfated rFIX material after purification is at least 49%. In another example of the present invention, the percentage of fully phosphorylated and sulfated rFIX material after purification is at least 53%.

According to the present invention, the term "recombinant blood coagulation factor IX" does not underlie a specific restriction and may include any rFIX, heterologous or naturally occurring, obtained via recombinant DNA technology, or a biologically active derivative thereof. In certain embodiments, the term encompasses proteins and nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity, over a region of at least about 25, 50, 100, 200, 300, 400, 450, or more amino acids (up to the full length sequence), to a polypeptide encoded by a referenced nucleic acid or an amino acid sequence described herein; (2) specifically bind to antibodies, e.g., polyclonal antibodies, raised against an immunogen comprising a referenced amino acid sequence as described herein immunogenic fragments thereof, and conservatively modified variants thereof (3) specifically hybridize under stringent hybridization conditions to a nucleic acid encoding a referenced amino acid sequence as described herein, and conservatively modified variants thereof (4) have a nucleic acid sequence that has greater than about 95%, greater than about 96%, 97%, 98%, 99%, or higher nucleotide sequence identity, over a region of at least about 25, 50, 100, 150, 200, 250, 500, 1000, 2000, 2500 or more nucleotides (up to the full length sequence), to a reference nucleic acid sequence as described herein. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention are recombinant molecules (e.g., heterologous and encoding the wild type sequence or a variant thereof, or non-naturally occurring). Reference polynucleotide and polypeptide sequences include, e.g., Accession Nos. NM_000133; BC109214; BC109215; J00137PM11309; and J00136 (see, e.g., Mammalian Gene Collection Program Team, PNAS USA 99:16899-16903 (2002); Autin et al., J. Thromb. Haemost. 3:2044-2056 (2005); Jaye et al., NAR 11:2325-2335 (1983); McGraw et al., PNAS 82:2847-2851 (1985) Choo et al., Nature 299:178-180 (1982); and Kurachi and Davie, PNAS 79:6461-6464 (1982)). In one embodiment, there are 2 point mutations in the Factor IX nucleic acid sequence as compared to NM_000133: position 57: CTT->CTC Leu->Leu (no amino acid change); and position 580: ACT->GCT Thr->Ala (amino acid change) (SEQ ID NOS:3 and 4).

In one embodiment, a polynucleotide sequence encoding Factor IX comprises the following coding sequence found under accession number NM_000133:

```
                                                            (SEQ ID NO:2)
accactttca caatctgcta gcaaaggtt atg cag cgc gtg aac atg atc atg        53
                                 Met Gln Arg Val Asn Met Ile Met gca gaa tca cca ggc ctc atc acc atc tgc ctt tta gga tat cta ctc       101
Ala Glu Ser Pro Gly Leu Ile Thr Ile Cys Leu Leu Gly Tyr Leu Leu agt gct gaa tgt aca gtt ttt ctt gat cat gaa aac gcc aac aaa att       149
Ser Ala Glu Cys Thr Val Phe Leu Asp His Glu Asn Ala Asn Lys Ile ctg aat cgg cca aag agg tat aat tca ggt aaa ttg gaa gag ttt gtt       197
Leu Asn Arg Pro Lys Arg Tyr Asn Ser Gly Lys Leu Glu Glu Phe Val caa ggg aac ctt gag aga gaa tgt atg gaa gaa aag tgt agt ttt gaa       245
Gln Gly Asn Leu Glu Arg Glu Cys Met Glu Glu Lys Cys Ser Phe Glu gaa gca cga gaa gtt ttt gaa aac act gaa aga aca act gaa ttt tgg       293
Glu Ala Arg Glu Val Phe Glu Asn Thr Glu Arg Thr Thr Glu Phe Trp aag cag tat gtt gat gga gat cag tgt gag tcc aat cca tgt tta aat       341
Lys Gln Tyr Val Asp Gly Asp Gln Cys Glu Ser Asn Pro Cys Leu Asn ggc ggc agt tgc aag gat gac att aat tcc tat gaa tgt tgg tgt ccc       389
Gly Gly Ser Cys Lys Asp Asp Ile Asn Ser Tyr Glu Cys Trp Cys Pro ttt gga ttt gaa gga aag aac tgt gaa tta gat gta aca tgt aac att       437
Phe Gly Phe Glu Gly Lys Asn Cys Glu Leu Asp Val Thr Cys Asn Ile aag aat ggc aga tgc gag cag ttt tgt aaa aat agt gct gat aac aag       485
Lys Asn Gly Arg Cys Glu Gln Phe Cys Lys Asn Ser Ala Asp Asn Lys gtg gtt tgc tcc tgt act gag gga tat cga ctt gca gaa aac cag aag       533
Val Val Cys Ser Cys Thr Glu Gly Tyr Arg Leu Ala Glu Asn Gln Lys tcc tgt gaa cca gca gtg cca ttt cca tgt gga aga gtt tct gtt tca       581
Ser Cys Glu Pro Ala Val Pro Phe Pro Cys Gly Arg Val Ser Val Ser caa act tct aag ctc acc cgt gct gag act gtt ttt cct gat gtg gac       629
Gln Thr Ser Lys Leu Thr Arg Ala Glu Thr Val Phe Pro Asp Val Asp tat gta aat tct act gaa gct gaa acc att ttg gat aac atc act caa       677
Tyr Val Asn Ser Thr Glu Ala Glu Thr Ile Leu Asp Asn Ile Thr Gln agc acc caa tca ttt aat gac ttc act cgg gtt gtt ggt gga gaa gat       725
Ser Thr Gln Ser Phe Asn Asp Phe Thr Arg Val Val Gly Gly Glu Asp
```

-continued

| | | |
|---|---|---|
| gcc aaa cca ggt caa ttc cct tgg cag gtt gtt ttg aat ggt aaa gtt<br>Ala Lys Pro Gly Gln Phe Pro Trp Gln Val Val Leu Asn Gly Lys Val | 773 | |
| gat gca ttc tgt gga ggc tct atc gtt aat gaa aaa tgg att gta act<br>Asp Ala Phe Cys Gly Gly Ser Ile Val Asn Glu Lys Trp Ile Val Thr | 821 | |
| gct gcc cac tgt gtt gaa act ggt gtt aaa att aca gtt gtc gca ggt<br>Ala Ala His Cys Val Glu Thr Gly Val Lys Ile Thr Val Val Ala Gly | 869 | |
| gaa cat aat att gag gag aca gaa cat aca gag caa aag cga aat gtg<br>Glu His Asn Ile Glu Glu Thr Glu His Thr Glu Gln Lys Arg Asn Val | 917 | |
| att cga att att cct cac cac aac tac aat gca gct att aat aag tac<br>Ile Arg Ile Ile Pro His His Asn Tyr Asn Ala Ala Ile Asn Lys Tyr | 965 | |
| aac cat gac att gcc ctt ctg gaa ctg gac gaa ccc tta gtg cta aac<br>Asn His Asp Ile Ala Leu Leu Glu Leu Asp Glu Pro Leu Val Leu Asn | 1013 | |
| agc tac gtt aca cct att tgc att gct gac aag gaa tac acg aac atc<br>Ser Tyr Val Thr Pro Ile Cys Ile Ala Asp Lys Glu Tyr Thr Asn Ile | 1061 | |
| ttc ctc aaa ttt gga tct ggc tat gta agt ggc tgg gga aga gtc ttc<br>Phe Leu Lys Phe Gly Ser Gly Tyr Val Ser Gly Trp Gly Arg Val Phe | 1109 | |
| cac aaa ggg aga tca gct tta gtt ctt cag tac ctt aga gtt cca ctt<br>His Lys Gly Arg Ser Ala Leu Val Leu Gln Tyr Leu Arg Val Pro Leu | 1157 | |
| gtt gac cga gcc aca tgt ctt cga tct aca aag ttc acc atc tat aac<br>Val Asp Arg Ala Thr Cys Leu Arg Ser Thr Lys Phe Thr Ile Tyr Asn | 1205 | |
| aac atg ttc tgt gct ggc ttc cat gaa gga ggt aga gat tca tgt caa<br>Asn Met Phe Cys Ala Gly Phe His Glu Gly Gly Arg Asp Ser Cys Gln | 1253 | |
| gga gat agt ggg gga ccc cat gtt act gaa gtg gaa ggg acc agt ttc<br>Gly Asp Ser Gly Gly Pro His Val Thr Glu Val Glu Gly Thr Ser Phe | 1301 | |
| tta act gga att att agc tgg ggt gaa gag tgt gca atg aaa ggc aaa<br>Leu Thr Gly Ile Ile Ser Trp Gly Glu Glu Cys Ala Met Lys Gly Lys | 1349 | |
| tat gga ata tat acc aag gta tcc cgg tat gtc aac tgg att aag gaa<br>Tyr Gly Ile Tyr Thr Lys Val Ser Arg Tyr Val Asn Trp Ile Lys Glu | 1397 | |
| aaa aca aag ctc act taa tgaaagatgg atttccaagg ttaattcatt<br>Lys Thr Lys Leu Thr | 1445 | |
| | (SEQ ID NO:1) | |
| ggaattgaaa attaacaggg cctctcacta actaatcact ttcccatctt tgttagatt | 1505 | |
| tgaatatata cattctatga tcattgcttt ttctctttac aggggagaat ttcatatttt | 1565 | |
| acctgagcaa attgattaga aaatggaacc actagaggaa tataatgtgt taggaaatta | 1625 | |
| cagtcatttc taagggccca gcccttgaca aaattgtgaa gttaaattct ccactctgtc | 1685 | |
| catcagatac tatggttctc cactatggca actaactcac tcaattttcc ctccttagca | 1745 | |
| gcattccatc ttcccgatct tctttgcttc tccaaccaaa acatcaatgt ttattagttc | 1805 | |
| tgtatacagt acaggatctt tggtctactc tatcacaagg ccagtaccac actcatgaag | 1865 | |
| aaagaacaca ggagtagctg agaggctaaa actcatcaaa aacactactc cttttcctct | 1925 | |
| accctattcc tcaatctttt accttttcca aatcccaatc cccaaatcag ttttttctctt | 1985 | |
| tcttactccc tctctcccctt ttaccctcca tggtcgttaa aggagagatg gggagcatca | 2045 | |
| ttctgttata cttctgtaca cagttataca tgtctatcaa acccagactt gcttccatag | 2105 | |
| tggagacttg cttttcagaa catagggatg aagtaaggtg cctgaaaagt ttggggggaaa | 2165 | |
| agtttctttc agagagttaa gttatttttat atatataata tatatataaa atatataata | 2225 | |
| tacaatataa atatatagtg tgtgtgtgta tgcgtgtgtg tagacacaca cgcatacaca | 2285 | |
| catataatgg aagcaataag ccattctaag agcttgtatg gttatggagg tctgactagg | 2345 | |
| catgatttca cgaaggcaag attggcatat cattgtaact aaaaaagctg acattgaccc | 2405 | |
| agacatattg tactctttct aaaaataata ataataatgc taacagaaag aagagaaccg | 2465 | |

-continued

```
ttcgtttgca atctacagct agtagagact ttgaggaaga attcaacagt gtgtcttcag    2525
cagtgttcag agccaagcaa gaagttgaag ttgcctagac cagaggacat aagtatcatg    2585
tctcctttaa ctagcatacc ccgaagtgga gaagggtgca gcaggctcaa aggcataagt    2645
cattccaatc agccaactaa gttgtcctttt tctggtttcg tgttcaccat ggaacatttt    2705
gattatagtt aatccttcta tcttgaatct tctagagagt tgctgaccaa ctgacgtatg    2765 tttcccttttg tgaattaata aactggtgtt ctggttcat.
```

The term fully phosphorylated and sulfated rFIX refers to the degree of phosphorylation and sulfation as identified by determining the percentage of fully phosphorylated and sulfated rFIX by mass spectrometry (MS), e.g., electrospray-ionization quadrupole time of flight mass spectrometry (ESI-QTOF-MS). When measured with ESI-QTOF-MS, the percentage of fully phosphorylated and sulfated rFIX in a plasma derived FIX sample used as a standard is about 98%.

The term "recombinant" when used with reference, e.g., to a cell, or nucleic acid, protein, or vector, indicates that the cell, nucleic acid, protein or vector, has been modified by the introduction of a heterologous or non-naturally occurring nucleic acid or protein, or the alteration of a native nucleic acid or protein, or that the cell is derived from a cell so modified. Thus, for example, recombinant cells express genes that are not found within the native (non-recombinant) form of the cell, or express wild type and variant genes that are not in the native position in the genome of the cell, or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. In one example, this term refers to a nucleic acid that is not in its native position in the genome. In another example, the nucleic acid is recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein), or that it is a protein derived from a heterologous nucleic acid.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, or 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the complement of a test sequence. The definition also includes sequences that have deletions and/or additions, as well as those that have substitutions. As described below, the algorithms can account for gaps and the like. Identity exists over a region that is at least about 25 amino acids or nucleotides in length, or over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An example of algorithm that is suitable for determining percent sequence identity and sequence similarity are the BLAST and BLAST 2.0 algorithms, which are described in Altschul et al., Nuc. Acids Res. 25:33 89-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (B) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

As used herein, the term "biologically active derivative" includes any derivative of a protein, protein complex or polypeptide having substantially the same functional and/or biological properties of rFIX such as binding properties, and/or the same structural basis, such as a peptidic backbone. Minor deletions, additions and/or substitutions of amino acids of the polypeptide sequence of rFIX which are not altering the biological activity of said polypeptide are also included in the present application as biologically active derivatives.

The rFIX according to the present invention may be derived from any vertebrate, e.g. a mammal. In one specific example of the present invention, the rFIX is human FIX.

The rFIX according to the present invention may be produced by any method known in the art. This may include any method known in the art for the production of recombinant DNA by genetic engineering, e.g. via reverse transcription of RNA and/or amplification of DNA. Additionally, the recombinant DNA coding for rFIX, e.g. a plasmid, may also contain a DNA sequence encoding a selectable marker for selecting the cells which have been successfully transfected with the plasmid. In an example of the present invention, the plasmid may also confer resistance to a selectable marker, e.g. to the antibiotic drug G418, by delivering a resistance gene, e.g. the neo resistance gene conferring resistance to G418.

The production of rFIX may include any method known in the art for the introduction of recombinant DNA into eukaryotic cells by transfection, e.g. via electroporation or microinjection. For example, the recombinant expression of human FIX can be achieved by introducing an expression plasmid containing the human FIX encoding DNA sequence under the control of one or more regulating sequences such as a strong promoter, into a suitable host cell line by an appropriate transfection method resulting in cells having the introduced sequences stably integrated into the genome. The calcium-phosphate co-precipitation method is an example of a transfection method which may be used according to the present invention.

The production of rFIX may also include any method known in the art for the cultivation of said transformed cells, e.g. in a continuous or batchwise manner, and the expression of the rFIX, e.g. constitutive or upon induction. In one specific example of the present invention the nucleic acid coding for rFIX contained in the host organism of the present invention is expressed via an expression mode selected from the group consisting of induced, transient, and permanent expression. Any expression system known in the art or commercially available can be employed for the expression of a recombinant nucleic acid encoding rFIX, including the use of regulatory systems such as suitable, e.g. controllable, promoters, enhancers etc.

The production of rFIX may also include any method known in the art for the isolation of the protein, e.g. from the culture medium or by harvesting the transformed cells. For example, the rFIX-producing cells can be identified by isolating single-cell derived populations i.e. cell clones, via dilution after transfection and optionally via addition of a selective drug to the medium. After isolation the identified cell clones may be cultivated until confluency in order to enable the measurement of the rFIX content of the cell culture supernatant by enzyme-linked immuno-sorbent assay (ELISA) technique. Additionally, rFIX secreted by the cells may be identified for example by growing the cells in the absence of any growth promoting fetal bovine serum or components thereof. Vitamin K is added at appropriate concentrations to improve the functional properties of the rFIX protein. In one specific example of the present invention, the supernatant is harvested 24 hours after transfection. After identification, high rFIX producing cell clones may for example be further propagated and/or stored via cryopreservation. In one example of the present invention, the rFIX is co-expressed with vitamin K reductase complex subunit 1 (VKORC 1) and/or furin.

Additionally, the production of rFIX may include any method known in the art for the purification of rFIX, e.g. via anion exchange chromatography or affinity chromatography. In one embodiment rFIX can be purified from cell culture supernatants by semi-affinity calcium-dependent anion exchange chromatography, e.g. in an endotoxin-free system. The purified rFIX may be analyzed by methods known in the art for analyzing recombinant proteins, e.g. the ELISA technique. In addition, the protein integrity and activity may be assessed by measuring activated partial thromboplastin time (APTT) and by electrophoresis techniques including immuno-blotting.

Examples for the detection systems of the phosphorylation and sulfation of rFIX are known to a person skilled in the art. For example, degrees of phosphorylation and sulfation can be analyzed by LC-MS. It is within the knowledge of a person skilled in the art to choose the optimal parameters, such as buffer system, temperature and pH for the respective detection system to be used.

In one specific example of the present invention, the rFIX according to the present invention is expressed in a host cell type with the ability to perform the phosphorylation and sulfation as posttranslational modifications. The ability to phosphorylate and sulfate corresponding residues on rFIX of rFIX expressing host cell lines may be for example analyzed by mass-spectrometric analysis of the rFIX derived from these cell lines. For example, cell clones exhibiting the ability to add phosphorus-containing groups and sulfur-containing groups to the synthesized rFIX molecules, may be identified by determining the percentage of fully phosphorylated and sulfated rFIX by mass spectrometry (MS) after chromatographic purification of rFIX from cell culture supernatants. This may be accomplished, by e.g. binding rFIX protein to an anion exchange column and eluting fully carboxylated rFIX via the addition of Ca(II) ions. The conversion of collected rFIX preparations into peptides may be achieved, e.g. by tryptic digestion, optionally followed by an enzymatical removal of glycosidic residues. In the following, the peptides may be separated, e.g. by reversed phase HPLC, and analyzed by electro-spray-ionization quadrupole time of flight mass spectrometry (ESI-QTOF-MS). The degree of phosphorylated/non-phosphorylated and/or sulfated/non-sulfated peptide may be estimated by quantification of corresponding signals.

The host cell type according to the present invention may be any mammalian cell with the ability to perform the phosphorylation and sulfation as posttranslational modifications of rFIX. For example said mammalian cell is derived from a mammalian cell line, like for example a cell line selected from the group consisting of SkHep-, CHO-, HEK293-, and BHK-cells. In a specific example of the present invention, the rFIX is expressed in HEK293-derived cells.

The improved pharmacokinetic properties of higher phosphorylated and sulfated rFIX molecules may be confirmed e.g. in FIX-knockout mouse models.

According to the present invention, the in vivo recovery of rFIX after injection into an individuum is the observed peak plasma concentration relative to the expected peak concentration based on body weight or plasma volume. It is calculated from the maximum rFIX concentration rise from baseline and is expressed as U/dL or µg/dL increase per dose (U/kg or µg/kg) injected based on bodyweight. If based on plasma volume, the in-vivo recovery can be calculated as percentage of U found per U dosed (Shapiro et al., 2005b).

A further aspect of the present invention is the provision of a cell culture comprising cells expressing a rFIX resulting in a purified rFIX preparation having at least 25% of fully phosphorylated and sulfated rFIX.

The cell culture of the present invention may comprise any cell culture which contains cells capable of expressing rFIX and performing the phosphorylation and sulfation as posttranslational modifications of rFIX. Examples of suitable cells are listed above. In one specific example, the cell culture of the present invention is an eukaryotic cell culture characterized by producing one or more pharmacologically active rFIX having an improved in vivo recovery.

In one example of the present invention the cell culture of the present invention comprises a host organism as defined above.

There is no particular limitation to the media, reagents and conditions used for culturing the cells in the cell culture of the present invention including culturing the cells in a continuous or batchwise manner. In one example of the present invention the cells are cultured under serum-free or serum- and protein-free conditions. In a further example of the present invention conditions are employed under which cells which contain a recombinant nucleic acid coding for rFIX are selectively proliferated, e.g. by using a selective medium.

The desired rFIX protein which has been expressed by the cells of the selected host organism and which, dependent on the transfection/vector-system used, is contained in the cells or secreted into the medium for culturing cells, can be isolated/recovered from the cell culture using methods known in the art, as mentioned herein before.

In one specific example of the present invention, the cell culture according to the present invention comprises HEK293-derived cells. In another example of the present invention, the cells are switched to serum-free medium at confluency. Further, in another example of the present invention, the supernatants are harvested every day for at least two weeks.

The cell culture according to the present invention produces for example a rFIX resulting in a purified rFIX preparation having after purification at least 25% of fully phosphorylated and sulfated rFIX. In some embodiments, the cell culture produces about 50, 100, 150, 200, 250, 300, 350, 400, 450, 500, 550, 600, 650, 700, 750, 800, 850, 900, 1000, 1050, 1100, 1150, 1200, 1250, 1300, 1350, 1400, 1450, 1500, 1550, 1600, 1650, 1700, 1750, 1800, 1850, 1900, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 or about 5000 mU FIX per $10^6$ cells per day.

Another aspect of the present invention relates to a pharmaceutical composition comprising the above defined purified rFIX preparation having at least 25% of fully phosphorylated and sulfated rFIX for treating a bleeding disorder, e.g. a bleeding disorder associated with functional defects of FIX or deficiencies of FIX.

The expression "bleeding disorder associated with functional defects of FIX or deficiencies of FIX" as used herein includes bleeding disorders, wherein the cause of the bleeding disorder may be selected from the group consisting of a shortened in vivo-half-life of FIX, altered binding properties of FIX, genetic defects of FIX, and a reduced plasma concentration of FIX. Genetic defects of FIX comprise for example deletions, additions and/or substitution of bases in the nucleotide sequence encoding FIX whose absence, presence and/or substitution, respectively, has a negative impact on the activity of FIX. In one example of the present invention, the bleeding disorder is hemophilia B. Symptoms of such bleeding disorders include, e.g., severe epistaxis, oral mucosal bleeding, hemarthrosis, hematoma, persistent hematuria, gastrointestinal bleeding, retroperitoneal bleeding, tongue/retropharyngeal bleeding, intracranial bleeding, trauma-associated bleeding.

According to the methods of the present invention, a composition comprising the rFIX is administered by any parenteral (e.g., intravenously, intramuscularly, subcutaneously, or intraperitoneally) or non-parenteral route (e.g., orally). Pharmaceutical compositions comprising the rFIX described herein may also contain suitable excipients (e.g., carriers, buffers, and the like). Any suitable carrier known to those of ordinary skill in the art may be employed in the pharmaceutical compositions of this invention. Suitable carriers include, for example, water, saline, alcohol, a fat, a wax, a buffer, a solid carrier, such as mannitol, lactose, starch, magnesium stearate, sodium saccharine, talcum, cellulose, glucose, sucrose, and magnesium carbonate. Suitable buffers include, e.g., e.g., neutral buffered saline or phosphate buffered saline. Additional suitable excipients include, e.g., carbohydrates (e.g., glucose, mannose, sucrose or dextrans), mannitol, proteins, polypeptides or amino acids such as histindine or glycine, antioxidants, bacteriostats, chelating agents such as EDTA or glutathione, detergents (e.g., fatty acid esters of sorbitan polyethoxylates such as, for example, polysorbate 20, polysorbate 60, or polysorbate 80), solutes that render the formulation isotonic, hypotonic or weakly hypertonic with the blood of a recipient, suspending agents, thickening agents and/or preservatives. Alternatively, compositions of the present invention may be formulated as a lyophilizate.

The compositions described herein may be administered as part of a sustained release formulation (i.e., a formulation such as a capsule or sponge that effects a slow release of compound following administration). Such formulations may generally be prepared using well known technology (see, e.g., Coombes et al. (1996) Vaccine 14:1429-1438). Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound (see, e.g., WO 94/20078; WO 94/23701; and WO 96/06638). The amount of active compound contained within a sustained release formulation depends upon the site of implantation, the rate and expected duration of release and the nature of the condition to be treated or prevented.

The pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The present invention further relates to the use of a purified rFIX preparation having at least 25% of fully phosphorylated and sulfated rFIX in the manufacture of a medicament for treating a bleeding disorder.

One aspect of the present invention involves using the rFIX compositions described herein to treat, prevent or alleviate symptoms of the bleeding disorders associated with functional defects of FIX or deficiencies of FIX such as, for example, Hepatitis B. As used herein, a "subject" or a "patient" refers to any warm-blooded animal, such as, for example, a primate, preferably a human.

A "therapeutic dose" or "therapeutically effective amount" or "effective amount" of rFIX or a composition comprising rFIX is an amount of the rFIX or composition comprising rFIX which prevents, alleviates, abates, or reduces the severity of symptoms of bleeding disorders associated with functional defects of FIX or deficiencies of FIX.

Frequency of administration of the rFIX compositions described herein, as well as dosage, will vary from individual to individual, and may be readily established using standard techniques. Often 1, 2, 3, 4, or 5 doses are administered each week. In some cases, the doses are administered daily. In some cases, doses are administered 1, 2, 3, 4, or more times per day. Doses can also be administered on demand (e.g., following a trauma that causes bleeding in a subject or prior to a scheduled medical procedure expected to cause bleeding in a subject such as, for example surgery or dental work). A therapeutic dose is an amount of a compound that, when administered as described above, is capable of promoting an increased in vivo recovery of rFIX (e.g., as measured using the methods set forth in Example 3 below) or Factor IX activity (e.g., as measured by APTT assays as set forth in, e.g., Chen et al, Adv Ther. 2003 September-October; 20(5):231-6) following administration of the compositions to the individual. The compositions should also be capable of causing a response that leads to an improved clinical outcome (e.g., improved clotting time) in patients receiving the rFIX as compared to patients who do not receive such treatment. Such responses may generally be evaluated using samples obtained from a patient before and after treatment. Suitable dose sizes will vary with the body weight of the patient, type of hemorrhage to be treated or prevented, and the desired plasma FIX concentration, but will typically range from about 10-150, 20-100, 20-5-, or 40-50 International Units (IU) per kg body weight. An IU of FIX activity per kg body weight is typically equal to the FIX activity in 1 ml of fresh plasma and increases the FIX plasma concentration by 1%.

It is another object of the present invention to provide a method for treating a bleeding disorder comprising the step of administering a pharmaceutical composition comprising a purified rFIX preparation having at least 25% of fully phosphorylated and sulfated rFIX, e.g. for treating a bleeding disorder, e.g. to a patient in need thereof. In one example of the method for treating a bleeding disorder according to the present invention, the purified rFIX preparation having at least 25% of fully phosphorylated and sulfated rFIX, the pharmaceutical composition and the bleeding disorder are selected from the group consisting of the purified rFIX preparation as defined above, the pharmaceutical composition as defined above and the bleeding disorder as defined above.

The present invention will be further illustrated in the following examples, without any limitation thereto.

EXAMPLES

Example 1

Pharmacokinetics of De-Phosphorylated pdFIX in Comparison with pdFIX and rFIX-Product Benefix™

In order to trace altered in vivo recovery properties of FIX back to phosphorylation, the following study is performed: A pdFIX preparation is enzymatically de-phosphorylated using λ-phosphatase in order to compare the pharmacokinetics of the pdFIX molecule obtained after this procedure with Benefix™ and non-de-phosphorylated pdFIX in a FIX-knockout mouse model.

Briefly, pdFIX is de-phosphorylated with λ-phosphatase and purified via anion exchange chromatography. Benefix™, de-phosphorylated pdFIX, and pdFIX are formulated in the same buffer and administered intravenously (i.v.) to FIX-knockout mice at a dosage of 200 μg/kg and a volume of 10 ml/kg. Citrated plasma samples are taken after 15 min, 30 min, 1, 2, 4, and 16 hours. Each treatment is carried out with 10 animals per treatment and time point. FIX concentrations and activities are determined via ELISA and APTT. In vivo recovery is calculated from the highest FIX concentration value found within the first hour and is expressed as percentage of the administered dose. Half-life is calculated using a one-phase least square linear regression model of logarithmic transformed ELISA or APTT values. For each treatment the median values and the 95% confidence intervals of APTT and ELISA measurements are calculated. The results are shown in Table I for in vivo recovery and in Table II for half-life. Concerning recovery, the differences of pair wise comparisons of median values from both measurement methods are significant for Benefix™ in comparison to pdFIX as well as for de-phosphorylated pdFIX to pdFIX, but not significant between Benefix™ and de-phosphorylated pdFIX. Half-life is found to be slightly higher for the rFIX product Benefix™ than for pdFIX and de-phosphorylated pdFIX.

Similar in vivo recoveries of de-phosphorylated pdFIX and rFIX are found, which are both 40 to 60% lower than the observed in vivo recovery of pdFIX. It can be concluded from this study, that at least the enzymatic removal of the phosphate group at serine 158 from the FIX activation peptide, which is the only phosphorylation site within the FIX protein, converts pdFIX into a species with an in vivo recovery comparable to CHO-derived rFIX. Therefore, phosphorylation and eventually sulfation are valid targets when aiming at the development of cell lines for the production of an improved rFIX product.

TABLE I

In vivo recovery median values (%) of rFIX product Benefix ™, pdFIX, and enzymatically de-phosphorylated pdFIX found in FIX-knockout mice and as determined by ELISA and APTT clotting assay measurements.

| Treatment | % in vivo recovery based on ELISA | | % in vivo recovery based on APTT | |
|---|---|---|---|---|
| | Median values | 95% confidence interval | Median values | 95% confidence interval |
| Benefix ™ | 7.2 | 5.4 to 9.3 | 6.0 | 5.1 to 9.0 |
| Enzymatically dephosphorylated pdFIX | 9.5 | 8.1 to 10.8 | 8.4 | 6.9 to 11.3 |
| pdFIX | 17.0 | 13.1 to 20.0 | 15.0 | 13.6 to 20.6 |

TABLE II

Half-life median values (hours) of rFIX product Benefix ™, pdFIX, and enzymatically de-phosphorylated pdFIX found in FIX-knockout mice and as determined by ELISA and APTT clotting assay measurements.

| Treatment | Half life (hours) based on ELISA | | Half-life (hours) based on APTT | |
|---|---|---|---|---|
| | Median values | 95% confidence interval | Median values | 95% confidence interval |
| Benefix ™ | 6.5 | 5.9 to 7.2 | 8.9 | 7.9 to 12.0 |
| Enzymatically de-phosphorylated pdFIX | 6.1 | 5.7 to 6.7 | 6.7 | 6.3 to 7.4 |
| pdFIX | 5.1 | 4.5 to 5.8 | 6.6 | 6.0 to 7.6 |

Example 2

Recombinant Expression of FIX in Cell Culture and Screening for Cell Lines Exhibiting a High Degree of rFIX-phosphorylation and Sulfation The recombinant expression of human FIX is achieved by introducing an expression plasmid containing the human FIX encoding DNA sequence under the control of a strong promoter into the host cell line by an appropriate transfection method resulting in cells having the introduced sequences stably integrated into the genome. The transfection method used is a so-called calcium-phosphate co-precipitation method. The plasmid also confers resistance to a selectable marker antibiotic drug G418 by delivering the neo resistance gene.

For the identification of rFIX-producing cells, after transfection and addition of the selective drug to the medium, the cell suspension is diluted to enable isolation of single-cell derived populations, i.e. cell clones. After isolation, these cell clones are cultivated until confluency to enable the measurement of the rFIX content of the cell culture supernatant by ELISA technique. For that purpose, the cells are grown in the absence of any growth promoting fetal bovine serum or components thereof to ensure the identification of the cells secreting rFIX. To ensure a fully functional rFIX protein, vitamin K is added at appropriate concentrations. The supernatant is harvested after 24 hours and can be analyzed by ELISA technique. In addition, the protein integrity and activity is assessed by measuring APTT and by electrophoresis techniques including immuno-blotting. High rFIX producing cell clones are further propagated and stored via cryopreservation.

To identify cell clones exhibiting the ability to add phosphor and sulfate groups to the synthesized rFIX molecules, the percentage of fully phosphorylated and sulfated rFIX is determined by mass spectrometry (MS) after chromatographic purification of rFIX from cell culture supernatants. This is accomplished by binding rFIX protein to an anion exchange column and eluting fully carboxylated rFIX via the addition of Ca(II) ions as described in EP 0669342. Thus, collected rFIX preparations are converted to peptides by tryptic digestion, and glycosidic residues are removed enzymatically. These peptides are separated by reversed phase HPLC and are analyzed by ESI-QTOF-MS. The degree of phosphorylated and sulfated peptide is estimated by quantification of corresponding signals.

These techniques are used to generate cell lines producing rFIX. In this study, the recombinant expression of FIX is compared in 4 different host cell types (CHO, SkHep, BHK, HEK293) after stable transfection, and screening of appropriate producer cell lines. The percentages of phosphorylated and sulfated rFIX protein isoform from total rFIX after downstream purification are assessed by LC-MS and are shown in Table III. Because of these results, HEK293 is chosen as host cell line for improved rFIX isoform screening.

A broad panel of HEK293-derived rFIX producing cell lines is generated and screened for rFIX productivity and clotting activity by the established techniques. rFIX secreted from these cell clones is prepared and analyzed according to the above outlined procedures, and exhibits at least 25% phosphorylated and sulfated isoform of total rFIX. Some examples of HEK293-derived cell clones and their characteristic rFIX cell specific productivity rates determined by ELISA and APTT are listed in Table IV. Also listed are the percentages determined by LC-MS of fully phosphorylated and sulfated FIX isoform found after chromatograhic purification. As a control, the phosphorylation and sulfation content of a pdFIX product is determined by the same MS analytical procedure. The values of the CHO derived rFIX product Benefix™ taken from Kaufman et al., 1986, and Wasley et al., 1993, are also given in Table IV.

TABLE III

Comparison of percentages of phosphorylated and sulfated rFIX isoforms equally expressed in 4 different host cell types, purified from cell culture supernatants and determined by LC-MS.

| Host Cell type | Percentage of sulfated and phosphorylated rFIX isoform after usual purification | Percentage of sulfated and phosphorylated rFIX isoform after enrichment according to the present invention |
|---|---|---|
| CHO | 2-4% | not determined |
| BHK | 2% | not determined |
| SkHep | not detected | not determined |
| HEK293 | 10-20% | 25-56% |

TABLE IV

Cell specific production rates per day based on ELISA and APTT data, and percentages of fully phosphorylated and sulfated rFIX isoform produced by seven examples of HEK293-derived cell lines. The percentage of phosphorylated and sulfated FIX isoform found in pdFIX, and corresponding values of rFIX producing CHO clones taken from literature are also given.

|  | μg FIX/ $10^6$ cells/ day | mU FIX/ $10^6$ cells/ day | Percentage of fully phosphorylated and sulfated FIX material after purification |
|---|---|---|---|
| HEK293 clone #1 | 3.2 | 50 | 25% |
| HEK293 clone #2 | 1.6 | 130 | 28% |
| HEK293 clone #3 | 2.6 | 360 | 35% |
| HEK293 clone #4 | 10 | 1200 | 53% |
| HEK293 clone #5 | 25 | 2900 | 46% |
| HEK293 clone #6 | 26 | 3300 | 49% |
| HEK293 clone #7 | 19 | 1300 | 53% |
| HEK293 clone #8 | 4.6 | 570 | 56% |
| pdFIX | — | — | 98% |
| CHO-derived cell clones; values taken from literature | 2-4 | 90-300 | <1% |

Example 3

Pharmacokinetics of Improved, HEK293-derived rFIX in Comparison with pdFIX and rFIX Product Benefix™

The goal of the study is to confirm a significantly improved in vivo recovery but same half-life of HEK293 cell-derived rFIX in comparison to CHO cell-derived Benefix™ when administered to FIX-knockout mice. In addition, a pdFIX preparation should reveal similar pharmacokinetic properties as the HEK293-derived protein and serve as a control to show validity of the chosen animal model and to comply with literature data.

HEK293 cell lines producing high-phosphorylated and sulfated rFIX can be used for production of the test substance. rFIX can be purified from cell culture supernatants by semi-affinity calcium-dependent anion exchange chromatography (EP 0669342). Benefix™ and a pdFIX product are both commercially available. Degrees of phosphorylation and sulfation can be analyzed by LC-MS.

Briefly, rFIX and pdFIX forms can be administered i.v. in FIX-knockout mice at a dosage of 250 μg/kg and 10 ml/kg. Activity and concentration of administered FIX can be determined in plasma samples taken at multiple time points by ELISA and APTT clotting assay to calculate pharmacokinetic parameter values.

As shown in Example 2, several rFIX expressing HEK293 cell lines have been screened for performing high degrees of rFIX phosphorylation and sulfation. Frozen cells are stored in liquid nitrogen and cells can be suspended in DMEM/Ham's F12 medium containing 5-10% fetal bovine serum to larger culture systems like triple-T flasks. At confluency, the cells should be switched to vitamin K1-containing serum-free medium. Supernatants can be harvested every day for up to two weeks. rFIX can be purified via semi-affinity calcium-dependent anion exchange chromatography in an endotoxin-free system. Final product should be formulated in Benefix™ formulation buffer (10 mM L-histidine, 260 mM glycine, 1% sucrose, 0.005% Tween-80 in water, pH 6.8) at a concentration of 250 μg/10 ml and analyzed by LC-MS for degrees of phosphorylation and sulfation.

Benefix™ can be reconstituted in formulation buffer (10 mM L-histidine, 260 mM glycine, 1% sucrose, 0.005% Tween-80, pH 6.8) at a concentration of 250 μg/10 ml. The pdFIX can be reconstituted in Aqua bidest., dialyzed against Benefix™ formulation buffer and adjusted in this buffer to a concentration of 250 μg/10 ml. The pdFIX and Benefix™ should be analyzed by LC-MS for degrees of phosphorylation and sulfation.

A single dose of FIX preparations at 250 μg/kg and 10 ml/kg in Benefix™ formulation buffer can be administered via the lateral tail vein of FIX-knockout mice. Per time point and treatment, 5 male and 5 female animals should be used. Mice must be anesthetized, and blood can be collected by cardiac puncture at 15 min, 30 min, 1 hr, 4 hrs, 9 hrs post injection into sodium citrate to a final ratio of 1:10 (citrate: blood) and a final sodium citrate concentration of 3.8%. Plasma samples should be frozen immediately after centrifugation.

A control group of 5 male and 5 female mice administered with buffer only can be done at the first and the final time point.

All plasma samples can be tested for rFIX or pdFIX concentrations and activities by using ELISA and APTT clotting assay against FIX standards. Aliquots of the FIX preparations for injection should be used as reference substances to determine the actual injected amounts.

At least, the following pharmacokinetic parameters should be calculated to estimate improved pharmacokinetic properties:
  a. In vivo recovery: time point with highest concentration of ELISA or APTT values compared to injected dose (U/dL or μg/dL increase per U/kg or μg/kg injected).
  b. Elimination half-life (one-phase least square linear regression model of logarithmic transformed ELISA and APTT values).

Example 4

Transient Transfection and Co-expression of rVKORC1 in rFIX-Producing HEK293- and CHO-derived Cell Lines The expression of rFIX is achieved by introducing expression plasmids containing the human FIX encoding DNA sequence under the control of a strong viral promoter into mammalian host cell lines by an appropriate transfection method resulting in cells having the introduced sequences stably integrated into their genomes. The plasmids also confer resistance to a selectable marker drug by delivering the adequate resistance gene(s). In the case of CHO cells, which are able to grow only in presence of nucleotide precursors in the medium because of an enzyme defect of the nucleotide de-novo synthesis pathway, the expression of this enzyme, dihydrofolate-reductase (DHFR), is required. This enables co-amplification of the FIX gene by gradually increasing the concentration of methotrexate (MTX), which leads to an increase of copy numbers of both genes, encoding DHFR and rFIX, within the cell's genome. For that purpose, CHO derived cell clones have to be grown also in selective medium lacking nucleotides and nucleotide precursors.

For the identification of human rFIX producing cells, after transfection and addition of the selective drug(s) to the medium, the cell suspension is diluted to enable isolation of single-cell derived clones. After isolation, these cell clones are cultivated to confluency to enable measurement of rFIX content of the cell culture supernatant by ELISA technique. For that purpose, the cells have to be grown in the absence of any growth promoting fetal bovine serum or components thereof to ensure identification of by the cells secreted rFIX. To ensure a fully functional rFIX protein, vitamin K is added. The supernatant is harvested after 24 hours and analyzed by rFIX-specific ELISA technique. In addition, the protein's integrity and activity is assessed by measuring APTT.

Co-expression of rVKORC1 is accomplished by transient expression techniques using cell lines, which are already selected for rFIX expression. An expression plasmid comprising rVKORC1 cDNA is transfected into these cells without further clone selection. The supernatants are collected from the whole transfected cell pools, and rFIX content and activity are compared to negative controls and normalized for specific rFIX secretion rates to assess effects of rVKORC1 activity.

Materials and Methods:

Expression Vectors

The expression vectors are cloned according to standard cloning techniques. Briefly, pSV-DHFR is generated by inserting the PstI 1.5 kbp fragment of vector pAdD26SV (A)-3 (Scahill et al., 1983; vector is a gift by Dr. Hauser, GBF Germany) containing murine DHFR into a pSVβ vector (Clontech, Palo Alto, Calif.) providing the SV40 enhancer, early promoter and intron, where the β-galactosidase gene has been removed by NotI digestion, and a polylinker has been inserted. This vector has also been used to generate phact containing the human actin promoter and intron by exchanging the EcoRI/HindIII fragment with the EcoRI/HindIII fragment of phβAPr-1-βgal, which is also a gift by Dr. Hauser. phact-FIX containing wild-type human FIX cDNA with the ala148 polymorphism (McGraw et al., 1985) is generated by EcoRI digestion of pFIX-bluescript, which has been generated by inserting human FIX from a randomly primed human liver cDNA library into pBluescript (Stratagene, La Jolla, Calif.), and inserting the resulting fragment into phact partially digested with EcoRI.

The vector pCMV-FIX-neo is generated by inserting the EcoRI fragment of vector pFIX-bluescript into pCMVβ (Clontech), where the β-gal cDNA has been removed. Within this vector, the codon for Ala is exchanged to Thr by site-specific mutagenesis via PCR, changing the naturally occurring polymorphism of Ala148 to Thr148. The PCR product is re-inserted into the same vector again. The EcoRI fragment of this vector is cloned into pcDNA3.1 (Invitrogen, Carlsbad, Calif.) to yield pCMV-FIX-neo.

The vector pCMV-VKORC1-EDHpro is generated by using the vector pCEP4-VKORC1 (kindly provided by Prof. Oldenburg, for description see Rost et al., 2004) as a template for PCR. The PCR product containing the rVKORC1 cDNA is cloned into the pCMV-EDHpro vector (Herlitschka et al., 1996).

Cell Culture and Transfections

CHO DUKX/DXB11 cells were obtained from Columbia University (New York, N.Y.) and were cultivated in DMEM/Ham's F12 (1:1) mix (Invitrogen) supplemented with 5% fetal bovine serum (PAA, Linz, Austria), desoxy-adenosine, adenosine and thymidine (all from Sigma, St. Louis, Mo.) and L-Glutamine (Invitrogen) and penicillin/streptomycin (Invitrogen). HEK293 cells (ATCC No. CRL-1573) are cultivated in DMEM/Ham's F12 (1:1) mix supplemented with 5% fetal bovine serum and L-Glutamine and penicillin/streptomycin. For stable transfections, a calcium-phosphate co-precipitation method is used. CHOrFIX cells are generated by co-transfection with the linearized plasmids phact-FIX and pSV-DHFR and by selection in DMEM/Ham's F12 (1:1) mix without hypoxanthine, glycine, and thymidine (Invitrogen) supplemented with 5% dialyzed FBS (PAA). For gene amplification, MTX (Ebewe, Unterach, Austria) is added in stepwise increased concentrations beginning with 10 nM up to 200 nM. HEK293 cells are transfected with linearized plasmid pCMV-FIX-neo and selected in medium containing 500 µg/ml G418 (Invitrogen). Cell clones are isolated by limited dilution cloning techniques either manually or using a flow cytometric cell sorting technique.

FIX secretion into cell culture supernatants is detected by exchanging the growth medium for serum-free medium supplemented with 10 µg/ml vitamin K1 (Sigma). Supernatants are collected and. FIX concentrations are determined by ELISA and clotting assay (APTT). For the calculation of specific secretion rates, cell numbers are counted using a CASY cell counter (Schärfe Systems, Reutlingen, Germany).

For transient co-expression experiments, the non-linearized plasmid pCMV-VKORC1-EDHPro is transfected using Lipofectamine 2000 reagent (Invitrogen). The same vector without rVKORC1 cDNA is used as negative control.

Analytical Methods

ELISAs are performed using a polyclonal rabbit anti-human FIX (Accurate Chemical, Westbury, N.Y.) in a 1:40000 dilution as primary antibody, and a polyclonal goat anti-human FIX horseradish-peroxidase conjugate as detection antibody. As a standard, a human pd FIX (Enzyme Research Laboratories, S. Lafayette, Ind.) is used. APTT is determined using a STA Compact automated coagulometer (Diagnostica Stago, Asnieres, France) by diluting FIX-samples into FIX deficient plama. All reagents for clotting are from Baxter, Vienna, Austria.

Results

Two stable rFIX-producing cell lines, one CHO- and one HEK293-derived, are subjected to transient transfections with the expression vector pCMV-VKORC1-EDHpro carrying a cDNA encoding human VKORC1. As controls, the empty vector pCMV-EDHpro and the stable rFIX-expressing cell line are used. After transient transfections, the cells are left overnight in serum-containing medium. The cells are washed with PBS and cultivated for 24 hours in serum-free medium, then the supernatants are harvested. rFIX expression and secretion into the medium is monitored by immunochemical and coagulation diagnosis methods measuring antigen level or clotting activity. To estimate effects on cellular productivity, the secretion rates are calculated on the basis of product concentration per cell number and 24 hours.

HEK293 cells expressing rFIX shows a 2.7-fold mean increase of specific secretion rates and a 2.9-fold increase of rFIX-concentrations after rVKORC1 transfection in comparison to the empty vector control. These values are based on APTT measurements. ELISA values shows a 2.0-fold increase of concentrations, and a 1.8-fold increase of specific productivities.

For the CHO-derived rFIX-producer cell line, a 1.5-fold increase of ELISA-titers, and a 1.2-fold increase of ELISA-based specific secretion rates are observed. APTT-calculated secretion rates are 1.4-fold higher, and APTT-measured FIX concentrations 1.7-fold.

REFERENCES

Arruda, V. R., Hagstrom, J. N., Deitch, J., Heiman-Patterson, T., Camire, R. M., Chu, K., Fields, P. A., Herzog, R. W., Couto, L. B., Larson, P. J., and High, K. A., 2001. Posttranslational modifications of recombinant myotube-synthesized human factor IX. Blood 97, 130-138.

Bjorkman, S., Shapiro, A. D., and Berntorp, E., 2001. Pharmacokinetics of recombinant factor IX in relation to age of the patient: implications for dosing in prophylaxis. Haemophilia 7, 133-139.

Bond, M., Jankowski, M., Patel, H., Karnik, S., Strang, A., Xu, B., Rouse, J., Koza, S., Letwin, B., Steckert, J., Amphlett, G., and Scoble, H., 1998. Biochemical characterization of recombinant factor IX. Semin. Hematol. 35, 11-17.

Brinkhous, K. M., Sigman, J. L., Read, M. S., Stewart, P. F., McCarthy, K. P., Timony, G. A., Leppanen, S. D., Rup, B. J., Keith, J. C., Jr., Garzone, P. D., and Schaub, R. G., 1996. Recombinant human factor IX: replacement therapy, prophylaxis, and pharmacokinetics in canine hemophilia B. Blood 88, 2603-2610.

Ewenstein, B. M., Joist, J. H., Shapiro, A. D., Hofstra, T. C., Leissinger, C. A., Seremetis, S. V., Broder, M., Mueller-Velten, G., and Schwartz, B. A., 2002. Pharmacokinetic analysis of plasma-derived and recombinant F IX concentrates in previously treated patients with moderate or severe hemophilia B. Transfusion 42, 190-197.

Franck, N., Le Seyec, J., Guguen-Guillouzo, C., and Erdtmann, L., 2005. Hepatitis C virus NS2 protein is phosphorylated by the protein kinase CK2 and targeted for degradation to the proteasome. J. Virol. 79, 2700-2708.

Harrison, S., Adamson, S., Bonam, D., Brodeur, S., Charlebois, T., Clancy, B., Costigan, R., Drapeau, D., Hamilton, M., Hanley, K., Kelley, B., Knight, A., Leonard, M., McCarthy, M., Oakes, P., Sterl, K., Switzer, M., Walsh, R., and Foster, W., 1998. The manufacturing process for recombinant factor IX. Semin. Hematol. 35, 4-10.

Herlitschka, S. E., Falkner, F. G., Schlokat, U., & Dorner, F., 1996. Overexpression of human prothrombin in permanent cell lines using a dominant selection/amplification fusion marker. Protein Expr. Purif., 8, 358-364.

Kaufman, R. J., 1998. Post-translational modifications required for coagulation factor secretion and function. Thromb. Haemost. 79, 1068-1079.

Kaufman, R. J., Wasley, L. C., Furie, B. C., Furie, B., and Shoemaker, C. B., 1986. Expression, purification, and characterization of recombinant gamma-carboxylated factor IX synthesized in Chinese hamster ovary cells. J. Biol. Chem. 261, 9622-9628.

Keith, J. C., Jr., Ferranti, T. J., Misra, B., Frederick, T., Rup, B., McCarthy, K., Faulkner, R., Bush, L., and Schaub, R. G., 1995. Evaluation of recombinant human factor IX: pharmacokinetic studies in the rat and the dog. Thromb. Haemost. 73, 101-105.

Kim, Y. M., Barak, L. S., Caron, M. G., and Benovic, J. L., 2002. Regulation of arrestin-3 phosphorylation by casein kinase II. J. Biol. Chem. 277, 16837-16846.

Kisker, C. T., Eisberg, A., and Schwartz, B., 2003. Prophylaxis in factor IX deficiency product and patient variation. Haemophilia 9, 279-284.

Larson, P. J. and High, K. A., 2001. Gene therapy for hemophilia B: AAV-mediated transfer of the gene for coagulation factor IX to human muscle. Adv. Exp. Med. Biol. 489, 45-57.

Lindsay, M., Gil, G. C., Cadiz, A., Velander, W. H., Zhang, C., and Van Cott, K. E., 2004. Purification of recombinant DNA-derived factor IX produced in transgenic pig milk and fractionation of active and inactive subpopulations. J. Chromatogr. A 1026, 149-157.

Manno, C. S., 2003. The promise of third-generation recombinant therapy and gene therapy. Semin. Hematol. 40, 23-28.

McCarthy, K., Stewart, P., Sigman, J., Read, M., Keith, J. C., Jr., Brinkhous, K. M., Nichols, T. C., and Schaub, R. G., 2002. Pharmacokinetics of recombinant factor IX after intravenous and subcutaneous administration in dogs and cynomolgus monkeys. Thromb. Haemost. 87, 824-830.

McGraw, R. A., Davis, L. M., Noyes, C. M., Lundblad, R. L., Roberts, H. R., Graham, J. B., & Stafford, D. W., 1985 Evidence for a prevalent dimorphism in the activation peptide of human coagulation factor IX. PNAS USA, 82, 2847-2851.

Poon, M. C., Lillicrap, D., Hensman, C., Card, R., and Scully, M. F., 2002. Recombinant factor IX recovery and inhibitor safety: a Canadian post-licensure surveillance study. Thromb. Haemost. 87, 431-435.

Ragni, M. V., Pasi, K. J., White, G. C., Giangrande, P. L., Courter, S. G., and Tubridy, K. L., 2002. Use of recombinant factor IX in subjects with haemophilia B undergoing surgery. Haemophilia. 8, 91-97.

Rost S., Fregin A., Ivaskevicius V., Conzelmann E., Hortnagel K., Pelz H. J., Lappegard K., Seifried E., Scharrer I., Tuddenham E. G., Muller C. R., Strom T. M., Oldenburg J., 2004. Mutations in VKORC1 cause warfarin resistance and multiple coagulation factor deficiency type 2. Nature February 5; 427(6974):537-41.

Roth, D. A., Kessler, C. M., Pasi, K. J., Rup, B., Courter, S. G., and Tubridy, K. L., 2001. Human recombinant factor IX: safety and efficacy studies in hemophilia B patients previously treated with plasma-derived factor IX concentrates. Blood 98, 3600-3606.

Scahill, S. J., Devos, R., Van der, H. J., & Fiers, W., 1983. Expression and characterization of the product of a human immune interferon cDNA gene in Chinese hamster ovary cells. PNAS USA, 80, 4654-4658;

Schaub, R., Garzone, P., Bouchard, P., Rup, B., Keith, J., Brinkhous, K., and Larsen, G., 1998. Preclinical studies of recombinant factor IX. Semin. Hematol. 35, 28-32.

Schwaab, R. and Oldenburg, J., 2001. Gene therapy of hemophilia. Semin. Thromb. Hemost. 27, 417-424.

Shapiro, A. D., Di Paola, J., Cohen, A., Pasi, K. J., Heisel, M. A., Blanchette, V. S., Abshire, T. C., Hoots, W. K., Lusher, J. M., Negrier, C., Rothschild, C., and Roth, D. A., 2005a. The safety and efficacy of recombinant human blood coagulation factor IX in previously untreated patients with severe or moderately severe hemophilia B. Blood 105, 518-525.

Shapiro, A. D., Korth-Bradley, J., and Poon, M.-C., 2005b. Use of pharmacokinetics in the coagulation factor treatment of patients with haemophilia. *Haemophilia* 11, 571-582.

VandenDriessche, T., Collen, D., and Chuah, M. K., 2001. Viral vector-mediated gene therapy for hemophilia. *Curr. Gene Ther.* 1, 301-315.

Wasley, L. C., Rehemtulla, A., Bristol, J. A., and Kaufman, R. J., 1993. PACE/furin can process the vitamin K-dependent pro-factor IX precursor within the secretory pathway. *J. Biol. Chem.* 268, 8458-8465.

White, G. C., Beebe, A., and Nielsen, B., 1997. Recombinant factor IX; *Thromb. Haemost.* 78, 261-265.

White, G. C., Pickens, E. M., Liles, D. K., and Roberts, H. R., 1998. Mammalian recombinant coagulation proteins: structure and function. *Transfus. Sci.* 19, 177-189.

All publications, patent publications, patents, and Genback Accession Nos. applications cited in this specification are herein incorporated by reference in their entirety for all purposes as if each individual publication, patent publication, or patent were specifically and individually indicated to be incorporated by reference.

What is claimed is:

1. A method of expressing a recombinant blood coagulation human factor IX (rFIX) having at least 90% sequence identity to SEQ IDNO:2, wherein at least 25% of the rFIX is fully phosphorylated and sulfated, the method comprising the step of expressing a nucleic acid encoding the rFIX into an HEK 293 host cell type, said host cell comprising proteins with the ability to perform phosphorylation and sulfation as posttranslational modifications, wherein said host cell expresses furin; thereby producing rFIX of which at least 25% is fully phosphorylated and sulfated.

2. The method of claim 1, wherein the rFIX is expressed in the presence of vitamin K.

3. The method of claim 1, wherein said nucleic acid encoding the rFIX comprises a promoter operably linked to a sequence that encodes said rFIX.

4. The method of claim 3, wherein said promoter is the CMV promoter.

5. The method of claim 1, wherein less than 98% of said rFIX is fully phosphorylated and sulfated.

6. The method of claim 1, wherein said rFIX comprises a T194A mutation.

* * * * *

SEQUENCE LISTING

```
<160> NUMBER OF SEQ ID NOS: 4

<210> SEQ ID NO 1
<211> LENGTH: 2804
<212> TYPE: DNA
<213> ORGANISM: Homo sapiens
<220> FEATURE:
<221> NAME/KEY: CDS
<222> LOCATION: (30)...(1415)

<400> SEQUENCE: 1
accactttca caatctgcta gcaaaggtt atg cag cgc gtg aac atg atc atg          53
                                Met Gln Arg Val Asn Met Ile Met
                                 1               5 gca gaa tca cca ggc ctc atc acc atc tgc ctt tta gga tat cta ctc         101
Ala Glu Ser Pro Gly Leu Ile Thr Ile Cys Leu Leu Gly Tyr Leu Leu
     10                  15                  20 agt gct gaa tgt aca gtt ttt ctt gat cat gaa aac gcc aac aaa att         149
Ser Ala Glu Cys Thr Val Phe Leu Asp His Glu Asn Ala Asn Lys Ile
 25                  30                  35                  40 ctg aat cgg cca aag agg tat aat tca ggt aaa ttg gaa gag ttt gtt         197
Leu Asn Arg Pro Lys Arg Tyr Asn Ser Gly Lys Leu Glu Glu Phe Val
                 45                  50                  55 caa ggg aac ctt gag aga gaa tgt atg gaa gaa aag tgt agt ttt gaa         245
Gln Gly Asn Leu Glu Arg Glu Cys Met Glu Glu Lys Cys Ser Phe Glu
             60                  65                  70 gaa gca cga gaa gtt ttt gaa aac act gaa aga aca act gaa ttt tgg         293
Glu Ala Arg Glu Val Phe Glu Asn Thr Glu Arg Thr Thr Glu Phe Trp
         75                  80                  85 aag cag tat gtt gat gga gat cag tgt gag tcc aat cca tgt tta aat         341
Lys Gln Tyr Val Asp Gly Asp Gln Cys Glu Ser Asn Pro Cys Leu Asn
     90                  95                 100 ggc ggc agt tgc aag gat gac att aat tcc tat gaa tgt tgg tgt ccc         389
Gly Gly Ser Cys Lys Asp Asp Ile Asn Ser Tyr Glu Cys Trp Cys Pro
105                 110                 115                 120 ttt gga ttt gaa gga aag aac tgt gaa tta gat gta aca tgt aac att         437
Phe Gly Phe Glu Gly Lys Asn Cys Glu Leu Asp Val Thr Cys Asn Ile
                125                 130                 135 aag aat ggc aga tgc gag cag ttt tgt aaa aat agt gct gat aac aag         485
Lys Asn Gly Arg Cys Glu Gln Phe Cys Lys Asn Ser Ala Asp Asn Lys
            140                 145                 150 gtg gtt tgc tcc tgt act gag gga tat cga ctt gca gaa aac cag aag         533
Val Val Cys Ser Cys Thr Glu Gly Tyr Arg Leu Ala Glu Asn Gln Lys
        155                 160                 165 tcc tgt gaa cca gca gtg cca ttt cca tgt gga aga gtt tct gtt tca         581
Ser Cys Glu Pro Ala Val Pro Phe Pro Cys Gly Arg Val Ser Val Ser
    170                 175                 180
```

-continued

```
caa act tct aag ctc acc cgt gct gag act gtt ttt cct gat gtg gac    629
Gln Thr Ser Lys Leu Thr Arg Ala Glu Thr Val Phe Pro Asp Val Asp
185             190                 195                 200 tat gta aat tct act gaa gct gaa acc att ttg gat aac atc act caa    677
Tyr Val Asn Ser Thr Glu Ala Glu Thr Ile Leu Asp Asn Ile Thr Gln
                205                 210                 215 agc acc caa tca ttt aat gac ttc act cgg gtt gtt ggt gga gaa gat    725
Ser Thr Gln Ser Phe Asn Asp Phe Thr Arg Val Val Gly Gly Glu Asp
            220                 225                 230 gcc aaa cca ggt caa ttc cct tgg cag gtt gtt ttg aat ggt aaa gtt    773
Ala Lys Pro Gly Gln Phe Pro Trp Gln Val Val Leu Asn Gly Lys Val
        235                 240                 245 gat gca ttc tgt gga ggc tct atc gtt aat gaa aaa tgg att gta act    821
Asp Ala Phe Cys Gly Gly Ser Ile Val Asn Glu Lys Trp Ile Val Thr
250                 255                 260 gct gcc cac tgt gtt gaa act ggt gtt aaa att aca gtt gtc gca ggt    869
Ala Ala His Cys Val Glu Thr Gly Val Lys Ile Thr Val Val Ala Gly
265                 270                 275                 280 gaa cat aat att gag gag aca gaa cat aca gag caa aag cga aat gtg    917
Glu His Asn Ile Glu Glu Thr Glu His Thr Glu Gln Lys Arg Asn Val
                285                 290                 295 att cga att att cct cac cac aac tac aat gca gct att aat aag tac    965
Ile Arg Ile Ile Pro His His Asn Tyr Asn Ala Ala Ile Asn Lys Tyr
            300                 305                 310 aac cat gac att gcc ctt ctg gaa ctg gac gaa ccc tta gtg cta aac    1013
Asn His Asp Ile Ala Leu Leu Glu Leu Asp Glu Pro Leu Val Leu Asn
        315                 320                 325 agc tac gtt aca cct att tgc att gct gac aag gaa tac acg aac atc    1061
Ser Tyr Val Thr Pro Ile Cys Ile Ala Asp Lys Glu Tyr Thr Asn Ile
330                 335                 340 ttc ctc aaa ttt gga tct ggc tat gta agt ggc tgg gga aga gtc ttc    1109
Phe Leu Lys Phe Gly Ser Gly Tyr Val Ser Gly Trp Gly Arg Val Phe
345                 350                 355                 360 cac aaa ggg aga tca gct tta gtt ctt cag tac ctt aga gtt cca ctt    1157
His Lys Gly Arg Ser Ala Leu Val Leu Gln Tyr Leu Arg Val Pro Leu
                365                 370                 375 gtt gac cga gcc aca tgt ctt cga tct aca aag ttc acc atc tat aac    1205
Val Asp Arg Ala Thr Cys Leu Arg Ser Thr Lys Phe Thr Ile Tyr Asn
            380                 385                 390 aac atg ttc tgt gct ggc ttc cat gaa gga ggt aga gat tca tgt caa    1253
Asn Met Phe Cys Ala Gly Phe His Glu Gly Gly Arg Asp Ser Cys Gln
        395                 400                 405 gga gat agt ggg gga ccc cat gtt act gaa gtg gaa ggg acc agt ttc    1301
Gly Asp Ser Gly Gly Pro His Val Thr Glu Val Glu Gly Thr Ser Phe
410                 415                 420 tta act gga att att agc tgg ggt gaa gag tgt gca atg aaa ggc aaa    1349
Leu Thr Gly Ile Ile Ser Trp Gly Glu Glu Cys Ala Met Lys Gly Lys
425                 430                 435                 440 tat gga ata tat acc aag gta tcc cgg tat gtc aac tgg att aag gaa    1397
Tyr Gly Ile Tyr Thr Lys Val Ser Arg Tyr Val Asn Trp Ile Lys Glu
                445                 450                 455 aaa aca aag ctc act taa tgaaagatgg atttccaagg ttaattcatt           1445
Lys Thr Lys Leu Thr
            460 ggaattgaaa attaacaggg cctctcacta actaatcact ttcccatctt ttgttagatt  1505 tgaatatata cattctatga tcattgcttt ttctctttac aggggagaat tcatattttt  1565 acctgagcaa attgattaga aaatggaacc actagaggaa tataatgtgt taggaaatta  1625 cagtcatttc taagggccca gcccttgaca aaattgtgaa gttaaattct ccactctgtc  1685
```

```
catcagatac tatggttctc cactatggca actaactcac tcaattttcc ctccttagca    1745
gcattccatc ttcccgatct tctttgcttc tccaaccaaa acatcaatgt ttattagttc    1805
tgtatacagt acaggatctt tggtctactc tatcacaagg ccagtaccac actcatgaag    1865
aaagaacaca ggagtagctg agaggctaaa actcatcaaa aacactactc cttttcctct    1925
accctattcc tcaatctttt accttttcca aatcccaatc cccaaatcag tttttctctt    1985
tcttactccc tctctccctt ttaccctcca tggtcgttaa aggagagatg gggagcatca    2045
ttctgttata cttctgtaca cagttataca tgtctatcaa acccagactt gcttccatag    2105
tggagacttg cttttcagaa catagggatg aagtaaggtg cctgaaaagt ttgggggaaa    2165
agtttctttc agagagttaa gttatttttat atatataata tatatataaa atatataata    2225
tacaatataa atatatagtg tgtgtgtgta tgcgtgtgtg tagacacaca cgcatacaca    2285
catataatgg aagcaataag ccattctaag agcttgtatg gttatggagg tctgactagg    2345
catgatttca cgaaggcaag attggcatat cattgtaact aaaaaagctg acattgaccc    2405
agacatattg tactctttct aaaaataata ataataatgc taacagaaag aagagaaccg    2465
ttcgtttgca atctacagct agtagagact ttgaggaaga attcaacagt gtgtcttcag    2525
cagtgttcag agccaagcaa gaagttgaag ttgcctagac cagaggacat aagtatcatg    2585
tctcctttaa ctagcatacc ccgaagtgga gaagggtgca gcaggctcaa aggcataagt    2645
cattccaatc agccaactaa gttgtccttt tctggttttcg tgttcaccat ggaacatttt    2705
gattatagtt aatccttcta tcttgaatct tctagagagt tgctgaccaa ctgacgtatg    2765 tttcccttttg tgaattaata aactggtgtt ctggttcat                         2804
```

<210> SEQ ID NO 2
<211> LENGTH: 461
<212> TYPE: PRT
<213> ORGANISM: Homo sapiens

<400> SEQUENCE: 2

```
Met Gln Arg Val Asn Met Ile Met Ala Glu Ser Pro Gly Leu Ile Thr
 1               5                  10                  15

Ile Cys Leu Leu Gly Tyr Leu Leu Ser Ala Glu Cys Thr Val Phe Leu
             20                  25                  30

Asp His Glu Asn Ala Asn Lys Ile Leu Asn Arg Pro Lys Arg Tyr Asn
         35                  40                  45

Ser Gly Lys Leu Glu Glu Phe Val Gln Gly Asn Leu Glu Arg Glu Cys
     50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175
```

```
Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 3
<211> LENGTH: 2804
<212> TYPE: DNA
<213> ORGANISM: Homo sapiens
<220> FEATURE:
<221> NAME/KEY: CDS
<222> LOCATION: (30)...(1415)

<400> SEQUENCE: 3
accactttca caatctgcta gcaaaggtt atg cag cgc gtg aac atg atc atg      53
                              Met Gln Arg Val Asn Met Ile Met
                                1               5 gca gaa tca cca ggc ctc atc acc atc tgc ctc tta gga tat cta ctc    101
Ala Glu Ser Pro Gly Leu Ile Thr Ile Cys Leu Leu Gly Tyr Leu Leu
    10                  15                  20 agt gct gaa tgt aca gtt ttt ctt gat cat gaa aac gcc aac aaa att    149
Ser Ala Glu Cys Thr Val Phe Leu Asp His Glu Asn Ala Asn Lys Ile
25                  30                  35                  40
```

-continued

| | |
|---|---|
| ctg aat cgg cca aag agg tat aat tca ggt aaa ttg gaa gag ttt gtt<br>Leu Asn Arg Pro Lys Arg Tyr Asn Ser Gly Lys Leu Glu Glu Phe Val<br>              45                    50                    55 | 197 |
| caa ggg aac ctt gag aga gaa tgt atg gaa gaa aag tgt agt ttt gaa<br>Gln Gly Asn Leu Glu Arg Glu Cys Met Glu Glu Lys Cys Ser Phe Glu<br>          60                    65                    70 | 245 |
| gaa gca cga gaa gtt ttt gaa aac act gaa aga aca act gaa ttt tgg<br>Glu Ala Arg Glu Val Phe Glu Asn Thr Glu Arg Thr Thr Glu Phe Trp<br>      75                    80                    85 | 293 |
| aag cag tat gtt gat gga gat cag tgt gag tcc aat cca tgt tta aat<br>Lys Gln Tyr Val Asp Gly Asp Gln Cys Glu Ser Asn Pro Cys Leu Asn<br>          90                    95                    100 | 341 |
| ggc ggc agt tgc aag gat gac att aat tcc tat gaa tgt tgg tgt ccc<br>Gly Gly Ser Cys Lys Asp Asp Ile Asn Ser Tyr Glu Cys Trp Cys Pro<br>105                    110                    115                    120 | 389 |
| ttt gga ttt gaa gga aag aac tgt gaa tta gat gta aca tgt aac att<br>Phe Gly Phe Glu Gly Lys Asn Cys Glu Leu Asp Val Thr Cys Asn Ile<br>                    125                    130                    135 | 437 |
| aag aat ggc aga tgc gag cag ttt tgt aaa aat agt gct gat aac aag<br>Lys Asn Gly Arg Cys Glu Gln Phe Cys Lys Asn Ser Ala Asp Asn Lys<br>                140                    145                    150 | 485 |
| gtg gtt tgc tcc tgt act gag gga tat cga ctt gca gaa aac cag aag<br>Val Val Cys Ser Cys Thr Glu Gly Tyr Arg Leu Ala Glu Asn Gln Lys<br>              155                    160                    165 | 533 |
| tcc tgt gaa cca gca gtg cca ttt cca tgt gga aga gtt tct gtt tca<br>Ser Cys Glu Pro Ala Val Pro Phe Pro Cys Gly Arg Val Ser Val Ser<br>170                    175                    180 | 581 |
| caa act tct aag ctc acc cgt gct gag gct gtt ttt cct gat gtg gac<br>Gln Thr Ser Lys Leu Thr Arg Ala Glu Ala Val Phe Pro Asp Val Asp<br>185                    190                    195                    200 | 629 |
| tat gta aat tct act gaa gct gaa acc att ttg gat aac atc act caa<br>Tyr Val Asn Ser Thr Glu Ala Glu Thr Ile Leu Asp Asn Ile Thr Gln<br>                    205                    210                    215 | 677 |
| agc acc caa tca ttt aat gac ttc act cgg gtt gtt ggt gga gaa gat<br>Ser Thr Gln Ser Phe Asn Asp Phe Thr Arg Val Val Gly Gly Glu Asp<br>                    220                    225                    230 | 725 |
| gcc aaa cca ggt caa ttc cct tgg cag gtt gtt ttg aat ggt aaa gtt<br>Ala Lys Pro Gly Gln Phe Pro Trp Gln Val Val Leu Asn Gly Lys Val<br>              235                    240                    245 | 773 |
| gat gca ttc tgt gga ggc tct atc gtt aat gaa aaa tgg att gta act<br>Asp Ala Phe Cys Gly Gly Ser Ile Val Asn Glu Lys Trp Ile Val Thr<br>250                    255                    260 | 821 |
| gct gcc cac tgt gtt gaa act ggt gtt aaa att aca gtt gtc gca ggt<br>Ala Ala His Cys Val Glu Thr Gly Val Lys Ile Thr Val Val Ala Gly<br>265                    270                    275                    280 | 869 |
| gaa cat aat att gag gag aca gaa cat aca gag caa aag cga aat gtg<br>Glu His Asn Ile Glu Glu Thr Glu His Thr Glu Gln Lys Arg Asn Val<br>                    285                    290                    295 | 917 |
| att cga att att cct cac cac aac tac aat gca gct att aat aag tac<br>Ile Arg Ile Ile Pro His His Asn Tyr Asn Ala Ala Ile Asn Lys Tyr<br>              300                    305                    310 | 965 |
| aac cat gac att gcc ctt ctg gaa ctg gac gaa ccc tta gtg cta aac<br>Asn His Asp Ile Ala Leu Leu Glu Leu Asp Glu Pro Leu Val Leu Asn<br>                315                    320                    325 | 1013 |
| agc tac gtt aca cct att tgc att gct gac aag gaa tac acg aac atc<br>Ser Tyr Val Thr Pro Ile Cys Ile Ala Asp Lys Glu Tyr Thr Asn Ile<br>          330                    335                    340 | 1061 |
| ttc ctc aaa ttt gga tct ggc tat gta agt ggc tgg gga aga gtc ttc<br>Phe Leu Lys Phe Gly Ser Gly Tyr Val Ser Gly Trp Gly Arg Val Phe<br>345                    350                    355                    360 | 1109 |

-continued

```
cac aaa ggg aga tca gct tta gtt ctt cag tac ctt aga gtt cca ctt    1157
His Lys Gly Arg Ser Ala Leu Val Leu Gln Tyr Leu Arg Val Pro Leu
                365                 370                 375 gtt gac cga gcc aca tgt ctt cga tct aca aag ttc acc atc tat aac    1205
Val Asp Arg Ala Thr Cys Leu Arg Ser Thr Lys Phe Thr Ile Tyr Asn
        380                 385                 390 aac atg ttc tgt gct ggc ttc cat gaa gga ggt aga gat tca tgt caa    1253
Asn Met Phe Cys Ala Gly Phe His Glu Gly Gly Arg Asp Ser Cys Gln
    395                 400                 405 gga gat agt ggg gga ccc cat gtt act gaa gtg gaa ggg acc agt ttc    1301
Gly Asp Ser Gly Gly Pro His Val Thr Glu Val Glu Gly Thr Ser Phe
410                 415                 420 tta act gga att att agc tgg ggt gaa gag tgt gca atg aaa ggc aaa    1349
Leu Thr Gly Ile Ile Ser Trp Gly Glu Glu Cys Ala Met Lys Gly Lys
425                 430                 435                 440 tat gga ata tat acc aag gta tcc cgg tat gtc aac tgg att aag gaa    1397
Tyr Gly Ile Tyr Thr Lys Val Ser Arg Tyr Val Asn Trp Ile Lys Glu
                445                 450                 455 aaa aca aag ctc act taa tgaaagatgg atttccaagg ttaattcatt           1445
Lys Thr Lys Leu Thr
            460 ggaattgaaa attaacaggg cctctcacta actaatcact ttcccatctt ttgttagatt  1505 tgaatatata cattctatga tcattgcttt ttctctttac aggggagaat ttcatatttt  1565 acctgagcaa attgattaga aaatggaacc actagaggaa tataatgtgt taggaaatta  1625 cagtcatttc taagggccca gcccttgaca aaattgtgaa gttaaattct ccactctgtc  1685 catcagatac tatggttctc cactatggca actaactcac tcaattttcc ctccttagca  1745 gcattccatc ttcccgatct tctttgcttc tccaaccaaa acatcaatgt ttattagttc  1805 tgtatacagt acaggatctt tggtctactc tatcacaagg ccagtaccac actcatgaag  1865 aaagaacaca ggagtagctg agaggctaaa actcatcaaa aacactactc cttttcctct  1925 accctattcc tcaatctttt acctttccca atcccaatc cccaaatcag ttttttctctt   1985 tcttactccc tctctccctt ttaccctcca tggtcgttaa aggagagatg gggagcatca  2045 ttctgttata cttctgtaca cagttataca tgtctatcaa acccagactt gcttccatag  2105 tggagacttg cttttcagaa catagggatg aagtaaggtg cctgaaaagt ttggggggaaa  2165 agtttctttc agagagttaa gttatttttat atatataata tatatataaa atatataata  2225 tacaatataa atatatagtg tgtgtgtgta tgcgtgtgtg tagacacaca cgcatacaca  2285 catataatgg aagcaataag ccattctaag agcttgtatg gttatggagg tctgactagg  2345 catgatttca cgaaggcaag attggcatat cattgtaact aaaaaagctg acattgaccc  2405 agacatattg tactctttct aaaaataata ataataatgc taacagaaag aagagaaccg  2465 ttcgtttgca atctacagct agtagagact ttgaggaaga attcaacagt gtgtcttcag  2525 cagtgttcag agccaagcaa gaagttgaag ttgcctagac cagaggacat aagtatcatg  2585 tctccttaa ctagcatacc ccgaagtgga aagggtgca gcaggctcaa aggcataagt    2645 cattccaatc agccaactaa gttgtccttt tctggtttcg tgttcaccat ggaacatttt  2705 gattatagtt aatccttcta tcttgaatct tctagagagt tgctgaccaa ctgacgtatg  2765 tttccctttg tgaattaata aactggtgtt ctggttcat                          2804
```

<210> SEQ ID NO 4
<211> LENGTH: 461
<212> TYPE: PRT

<213> ORGANISM: Homo sapiens

<400> SEQUENCE: 4

```
Met Gln Arg Val Asn Met Ile Met Ala Glu Ser Pro Gly Leu Ile Thr
  1               5                  10                  15

Ile Cys Leu Leu Gly Tyr Leu Leu Ser Ala Glu Cys Thr Val Phe Leu
             20                  25                  30

Asp His Glu Asn Ala Asn Lys Ile Leu Asn Arg Pro Lys Arg Tyr Asn
         35                  40                  45

Ser Gly Lys Leu Glu Glu Phe Val Gln Gly Asn Leu Glu Arg Glu Cys
     50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400
```

-continued

```
Glu Gly Gly Arg Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
    450                 455                 460
```